United States Patent
Norton (10) Patent No.: US 6,289,743 B1
(45) Date of Patent: Sep. 18, 2001

(54) SHOE TESTING APPARATUS AND METHOD OF USE

(76) Inventor: Craig Norton, 6830 Ridgewood Dr., Oakland, CA (US) 94611

( * ) Notice: Subject to any disclaimer, the term of this patent is extended or adjusted under 35 U.S.C. 154(b) by 0 days.

(21) Appl. No.: 09/282,441

(22) Filed: Mar. 31, 1999

(51) Int. Cl.[7] .............................. G01N 3/22; G01N 3/26
(52) U.S. Cl. ............................................................. 73/847
(58) Field of Search ............................... 73/799, 847, 27, 73/813, 7, 9, 172; 36/88

(56) References Cited

U.S. PATENT DOCUMENTS

| | | |
|---|---|---|
| 2,013,643 | 9/1935 | Bliss . |
| 2,638,776 | 5/1953 | Aines . |
| 2,799,162 | 7/1957 | Carlson . |
| 3,608,372 | 9/1971 | Hovey . |
| 3,620,071 | 11/1971 | Kelly . |
| 3,919,886 | 11/1975 | Chambley . |
| 4,096,733 | 6/1978 | Cohen . |
| 4,130,007 | 12/1978 | Hayashi . |
| 4,327,572 | 5/1982 | Pitman ........................... 73/7 |
| 4,432,223 | 2/1984 | Paquette ........................ 73/7 |
| 4,709,489 * | 12/1987 | Welter ........................... 36/27 |
| 4,958,522 | 9/1990 | McKinlay ...................... 73/847 |
| 5,079,995 | 1/1992 | Eberhardt ...................... 73/799 |
| 5,357,696 * | 10/1994 | Gray et al. .................... 73/172 |
| 5,567,884 | 10/1996 | Dickinson ..................... 73/813 |
| 5,632,104 * | 5/1997 | Zohar ............................ 36/88 |
| 5,722,103 * | 3/1998 | Walega .......................... 12/7 |

* cited by examiner

Primary Examiner—Benjamin R. Fuller
Assistant Examiner—Octavia Davis
(74) Attorney, Agent, or Firm—Tom Hamill, Jr.

(57) ABSTRACT

A testing and indexing apparatus and method for shoes is disclosed. A block is inserted into the interior of the shoe and clamps the heel portion of the sole fixed flat in relation to a plate. This plate is moved on rails until the ball or widest part of the shoe is set between laterally disposed clamps. The clamps are tightened on the ball of the shoe and the plate is fixed in position on the rails. Both the lateral clamping mechanism and the heel block clamp mechanism are attached to a generally rectangular base, however they are separate and the lateral clamping mechanism is axially rotatable along the axis of the clamped shoe and is attached to a torque wrench type device. Thus the shoe may be twisted axially to a pre-desired point and a reading taken to index the flexibility of the shoe in this dimension. This testing mechanism replicates the type of stress put on the shoe when worn walking or running during the midstance subphase when the entire body's weight is being transferred across the planar surface of the foot. People having foot pain from incorrect strides or faulty pronation in the midstance subphase of gait (at the point when the heel is striking the ground) require a shoe with less flexibility than others. Additionally, the device may be used to both index various brands of shoes in this manner and to determine when an old shoe needs to be replaced.

20 Claims, 7 Drawing Sheets

SHOE TESTING APPARATUS AND METHOD OF USE

BACKGROUND OF THE INVENTION

1. Field of the Invention

The present invention relates generally to testing devices and methods of use for same. More specifically, it relates to a testing device and method for shoes. Even more specifically, it relates to a testing device and method for determining the resistance to axial twisting motion in a shoe, and more particularly, to an apparatus and method that allows an indexing of the resistance of various shoes to such a twisting force commonly caused in a shoe during the user's use of the shoe. Even more particularly, it relates to a device and method of testing a shoe that allows the user to determine the proper shoe to purchase due to the unique stresses put on the shoe during the contact, midstance, and propulsion subphases of the user's stance in the case of abnormal pronation. The apparatus and method are especially adapted to effect the correct choice of shoe for individual walking and running characteristics.

2. Description of the Prior Art

Apparatus for axial stress testing of materials in the form of clamping, bending, and measuring apparatus are well known in the art of materials testing. The present invention, however, is unique in that its novel construction allows for quick and easy measuring of a shoe's resistance to axial twisting force.

Athletic shoes, in the last twenty five years, have progressed from canvas high-top "chucks" to today's computer designed, ergonomically proven footwear costing over a hundred dollars a pair. In this interval, the number of people using these athletic shoes, even for everyday wear, has skyrocketed. In this environment, many people make incorrect choices as to the type of shoe that they purchase. With differing body weights and stances during walking or running, some shoes are inappropriate for certain people in that they may flex too easily, thus leading to heel and muscle pain in the foot and lower extremety. The present invention allows for the testing of various shoes to determine the a quantative result that can be used to index the shoe in terms of its resistance to axial torque. In the present invention, the heel of the shoe to be tested is clamped in a fixed position, the portion of the shoe that would be proximate the metatarsal heads of the foot is clamped and torsionally rotated. A calibrated meter is provided to measure the amount of resistance in the shoe.

During a search at the U.S. Patent and Trademark Office, a number of prior art patents were discovered and they are discussed hereinbelow:

U.S. Pat. No. 2,013,643 issued to Elmer J. Bliss on Sep. 10, 1935 discloses a apparatus for the mechanical flexing of shoes. The device has no teaching of any axial twisting force, and the heel of the shoe in this invention is not secured.

In U.S. Pat. No. 2,638,776 issued to Andrew A. Aines on May 19, 1953 there is disclosed a mechanical footwear testing machine. In contrast to the present invention, the heel is not clamped to a fixed point, nor is the device seen to provide any axial torque to the footwear.

Another patent of interest is U.S. Pat. No. 2,799,162 issued to Harold C. R. Carlson on Jul. 16, 1957. This is an apparatus for testing torsion springs. Axial motion is applied to the torsion springs in this case, however, the right or left hand wound spring is placed snugly over an arbor and rests lightly against a pair of pins. A pointer is set, a crankshaft is turned, and then weights are rested on trays to bring the pointer back to zero. This is clearly dissimilar from the present invention, in that no clamping of a shoe heel on one end and lateral clamping of the ball portion of the shoe on the other, as is required by the present invention, is taught in Carlson.

In U.S. Pat. No. 3,608,372 issued to Emerson B. Hovey on Sep. 28, 1971 there is revealed a tester for shoes. The striker applies stress to the forward edge portion of the outsole. Unlike the present invention, there is no clamping of the heel portion and no measurement of the axial flex of the shoe under stress.

U.S. Pat. No. 3,620,071 issued to Louis E. Kelley et al. on Nov. 16, 1971 discloses a method and apparatus for testing materials for resilience and stress. In this device, a strip of material is stretched between two clamps and then twisted. When the twisting shaft is released, the oscillation period of the material is measured. Unlike the present invention, the clamping mechanisms of the Kelley et al. device attach at completely opposite ends of the test material and would not serve to test a shoe, which requires, for the purposes of biomechanical examination, that the heel of the shoe be fixed to a surface.

Next is U.S. Pat. No. 3,919,886 issued to Philip W. Chambley on Nov. 18, 1975. This relates to measuring yarn twist sets. Unlike the present invention, there is no teaching of the clamps required to test the axial rotation of a shoe.

In U.S. Pat. No. 4,096,733 issued to Arnold Cohen on Jun. 27, 1978 there is disclosed a device for testing footwear soles. This is clearly dissimilar from the instant invention in that there are no lateral clamps to hold the edges of the shoe proximate the ball of the foot, as are required in the present invention.

U.S. Pat. No. 4,130,007 issued to Hideki Hayashi on Dec. 19, 1978 teaches a footwear tester in which a footwear block fits inside the shoe to be tested and a prime mover simulates the motion of walking. There are no exterior clamps, no fixed heel portion, and no measurement of the axial resistance of the shoe to torque. Thus, the Hayashi patent is unlike the present invention.

U.S. Pat. No. 4,327,572 issued to F. Judson Pitman et al. on May 4, 1982 discloses a wear tester for shoes. This device drives the sole of a test shoe against an abrasive wear surface in a simulated motion of running. Thus it is clearly dissimilar from the present invention in that no resistance to axial torque is measured.

Another patent of interest is U.S. Pat. No. 4,432,223 issued to Elmer G. Paquette et al. on Feb. 21, 1984. This is a footwear testing apparatus and method and is unlike the present invention in that it is not concerned with measuring the axial resistance of the shoe's sole to torque.

In U.S. Pat. No. 4,958,522 issued to Peter R. McKinlay on Sep. 25, 1990 there is disclosed a shear stiffness tester. No laterally placed clamps are taught by this invention, nor is the instant invention's clamp that holds the heel downwardly against a fixed plate.

U.S. Pat. No. 5,079,955 issued to Allen C. Eberhardt on Jan. 14, 1992 is a method and apparatus for fatigue crack detection and propagation analysis. As in many of the above patents, the clamps required to biomechanically test the shoe are not shown and, additionally, the stress is applied perpendicular to the longitudinal axis of the test specimen.

Lastly, U.S. Pat. No. 5,567,884 issued to Gerard T. Dickinson et al. on Oct. 22, 1996 discloses a circuit board assembly torsion tester and method. Unlike the present invention, the lateral exterior clamps proximate the metatarsal area of the foot, required by the present invention for anatomical reasons, due to the midstance subphase of a user's stance; that is while the weight of the entire body is passing over the foot-these clamps are not taught. Neither is the clamp that holds the heel of the shoe to be tested firmly against a fixed platform.

Thus, while the foregoing body of prior art indicates it to be well known to use various clamps to test various materials under stress, the provision of a more simple and cost effective device as si described below is not contemplated. Nor does the prior art described above teach or suggest the novel clamps of the present invention to measure the resistance in a shoe to the longitudinal axial torsion stress created by walking or running in the sole of a shoe. The foregoing disadvantages are overcome by the unique downwardly fixed interior heel clamp and laterally disposed exterior metatarsal clamps of the present invention as will be made apparent from the following description thereof. Other advantages of the present invention over the prior art will also be rendered evident.

SUMMARY OF THE INVENTION

To achieve the foregoing and other advantages, the present invention, briefly described, provides a testing and indexing apparatus and method for shoes. A block is inserted into the interior of the shoe and clamps the heel portion of the sole fixed flat in relation to a plate. This plate is moved on rails until the ball or widest part of the shoe is set between laterally disposed clamps. The clamps are tightened on the ball of the shoe and the plate is fixed in position on the rails. Both the lateral clamping mechanism and the heel block clamp mechanism are attached to a generally rectangular base, however they are separate and the lateral clamping mechanism is axially rotatable along the axis of the clamped shoe and is attached to a torque wrench type device. Thus the shoe may be twisted axially to a pre-desired point and a reading taken to index the flexibility of the shoe in this dimension. This testing mechanism replicates the type of stress put on the shoe when worn walking or running during the midstance subphase when the entire body's weight is being transferred across the plantar surface of the foot. People having foot and lower extremity pain from incorrect strides or faulty pronation in the midstance subphase (at the point when the heel is striking the ground) require a shoe with less flexibility than others. Additionally, the device may be used to both index various brands of shoes in this manner and to determine when an old shoe needs to be replaced.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will form the subject matter of the claims appended hereto.

In this respect, before explaining at least one preferred embodiment of the invention in detail, it is to be understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which this disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

An object of the present invention is to provide a shoe testing apparatus and method of use wherein various brands of shoes or shoes of the same brand may be indexed according to their ability to resist twisting along their longitudinal axis.

It is still a further object of the present invention is to provide a shoe testing apparatus and method of use wherein a purchaser or user will be able to determine the stability of a shoe before wearing it.

Still a further object of the present invention is to provide a shoe testing apparatus and method of use including means for determining to what degree the shoe has lost the stability it once had, thus allowing the user to know when it should be replaced.

Still yet another object of the invention is to provide a shoe testing apparatus and method of use wherein the heel of the shoe is fixed by an internal block to an axially rigid plate to simulate the planted heel during the midstance subphase of a stride.

And yet still another object of the invention is to provide a shoe testing apparatus and method of use where the ball of the shoe, the widest portion proximate the metatarsal bones, is exteriorly clamped from both sides, and where these clamps are axially rotatable to simulate the twisting and flexing of the shoe during the midstance subphase of a stride.

Another object of the invention is to provide a shoe testing apparatus and method of use wherein the axially rotatable exteriorly clamped sections are connected to a torque meter that, when the shoe is twisted to a predetermined point, gives a reading that may be indexed against shoes of different brands, or of the shoe itself being tested sometime in the past.

It is another object of the present invention to provide a shoe testing apparatus which may be easily and efficiently manufactured and marketed.

It is a further objective of the present invention to provide shoe testing apparatus which is of durable and reliable construction.

An even further object of the present invention is to provide a shoe testing apparatus and method of use which is susceptible of a low cost of manufacture with regard to both materials and labor, and which accordingly is then susceptible of low prices of sale to the consuming public, thereby making such shoe testing apparatus available to the buying public.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein.

DESCRIPTION OF THE PREFERRED EMBODIMENT

With reference now to the drawings, a new and improved shoe testing apparatus and method for use embodying the principles and concepts of the present invention will be described.

Figure 1:
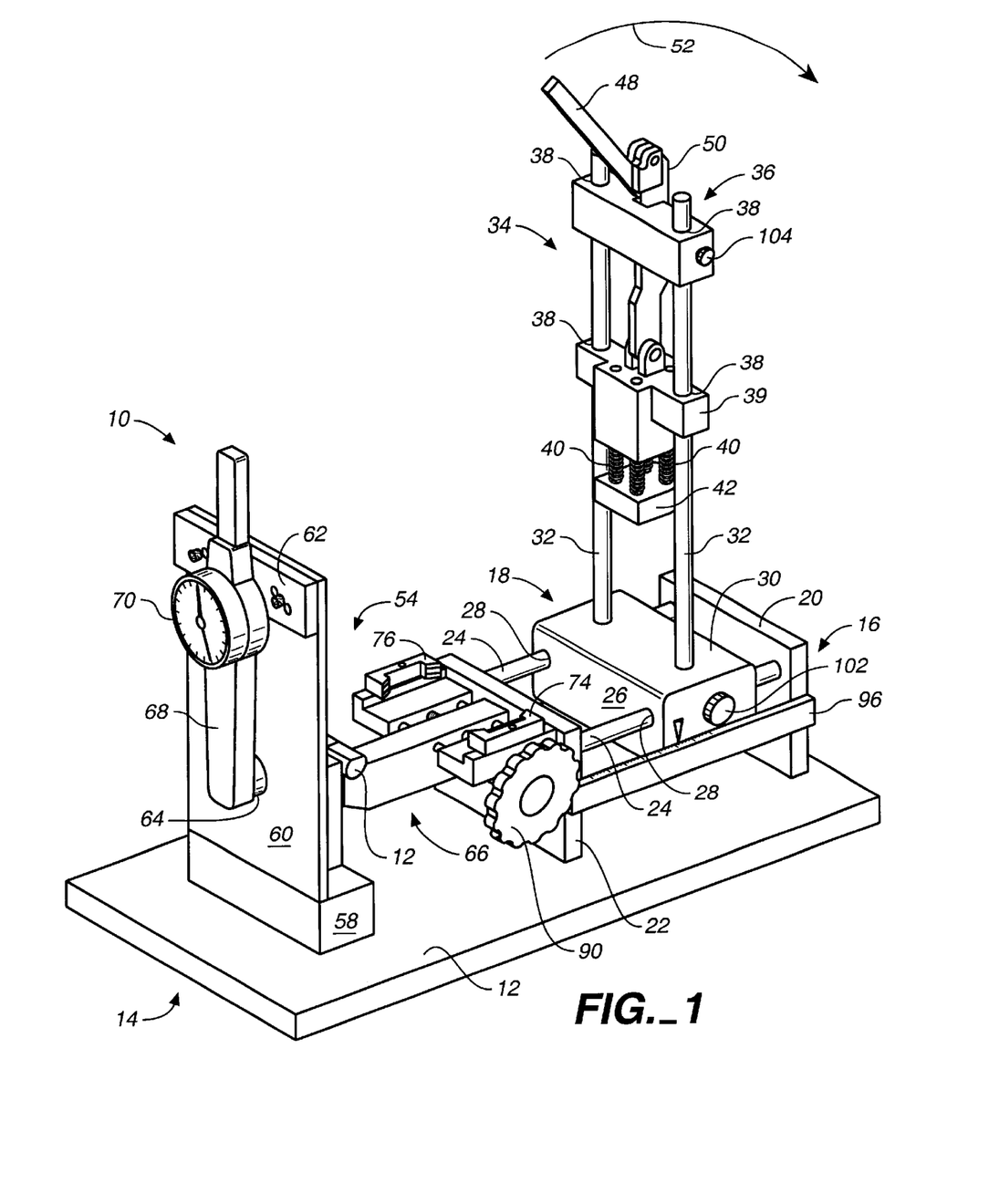
FIG. 1 is a perspective view showing the preferred embodiment of the present invention.

Referring first to FIG. 1, the major overall components of the present invention will be discussed. The entire shoe testing apparatus is generally indicated at 10. The apparatus 10 sits on a general rectangular base 12. To simplify matters, throughout this discussion, the apparatus 10 will be said to have a front indicated at 14 in the Figures, and a rear, indicated at 16 in the Figures. Most proximate the rear 16 of the apparatus 10 is the slidable heel block support portion 18. This consists of heel block support rear plate 20 and heel block support front plate 22. Extending between these two plates 20, 22 are rails 24. In the embodiment described herein, these are cylindrical in shape, but it should be understood that many other cross-sectional shapes, for example rectangles or I-bar cross sections could be envisioned by the skilled practitioner. Riding on these two rails 24 is the heel support plate 26. The rails 24 each extend through an aperture 28 in the heel support plate 26. Fixed into and extending above the upper heel support plate surface 30 are the vertical heel press block rails 32. Riding on and extending between these are first, the heel press block mechanism, generally indicated at 34 and, second, the over center cam lever carrier mechanism, generally indicated at 36. Both these mechanisms 34, 36 have vertical heel press block rail apertures, indicated at 38. As with rails 24, the vertical heel press block rails 32 could have a variety of cross sectional shapes. The heel press block mechanism 34 consists of three basic components, the upper heel press block rail and lever engaging portion 39, compression springs 40, and heel compression plate 42. The first overeater cam lever portion 44 is pivotally attached to the upper heel press block rail and lever engaging portion 39 as indicated at 46. A second overeater cam lever portion 48 is pivotally attached to the first overeater cam lever portion at 50. Thus when second overeater cam lever portion 48 is moved in the direction indicated by first directional arrow 52, first overeater cam lever portion 44 and the entire heel press block mechanism moves downward toward the upper heel support plate surface 30. The discussion will return to these elements of the invention during a description of the apparatus 10 in use.

Figure 2A:
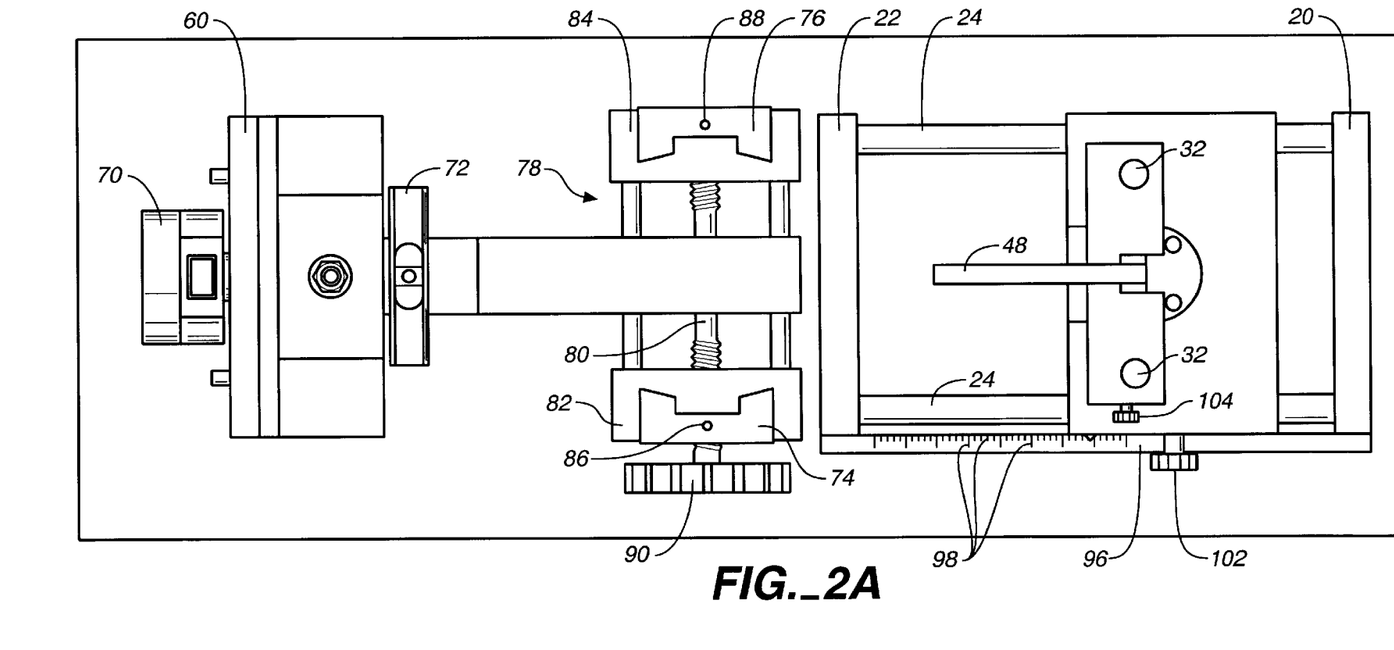
FIG. 2A is a top view of the preferred embodiment of the invention.

Still referring to FIG. 1, the partially axially tiltable shoe engaging portion is generally indicated at 54. It is located proximate the front 14 of the apparatus 10. In the preferred embodiment described herein, it has a fixed portion 56 consisting of a front block 58 attached to the base 12. Supported on the front block 58 is the torque support plate 60. Mounted on the upper portion of the torque support plate 60 is the travel stop support block 62. The torque support plate 60 has an aperture 64 extending therethrough. In FIG. 1, passing through aperture 64 is the axially tiltable shoe engaging portion generally indicated at 66. On the front side of the torque support plate 60, extending generally parallel thereto, is the torque meter 68, which has a dial 70. This will be discussed further below. The axially tiltable shoe engaging portion 66 also includes a level 72, a first and second lateral shoe engaging clamp 74, 76, and shoe engaging clamp adjustment means 78 (best seen in FIG. 2A), which consists of a partially threaded bolt 80, two fixed clamp carriers 82, 84, and first and second clamp pivots 86 and 88. The partial threaded bolt 80 moved the two fixed clamp carriers 82, 84 towards and away from one another by means of the adjustment knob 90. In the preferred embodiment described herein, the first and second lateral shoe engaging clamps are both C-shaped clamps that grip along the sides of the shoe S (discussed later). Other types of clamps, perhaps engaging on the top and bottom of the shoe could be used. The first and second lateral shoe engaging clamps could each be further adjustable, with means provided to move their jaws in relation to one another. Optionally, they could be a pivoted cup-like fit over the sides of the shoe S. The only important factor in the type of clamp used is that it grip the sides of the shoe S tightly enough to give an accurate reading when the torque is applied.

The discussion will now turn to the operation of the device and, afterwards, will describe the novel solution that the device engenders to the problem of incorrect stride or pronation when walking or running.

Figure 2B:
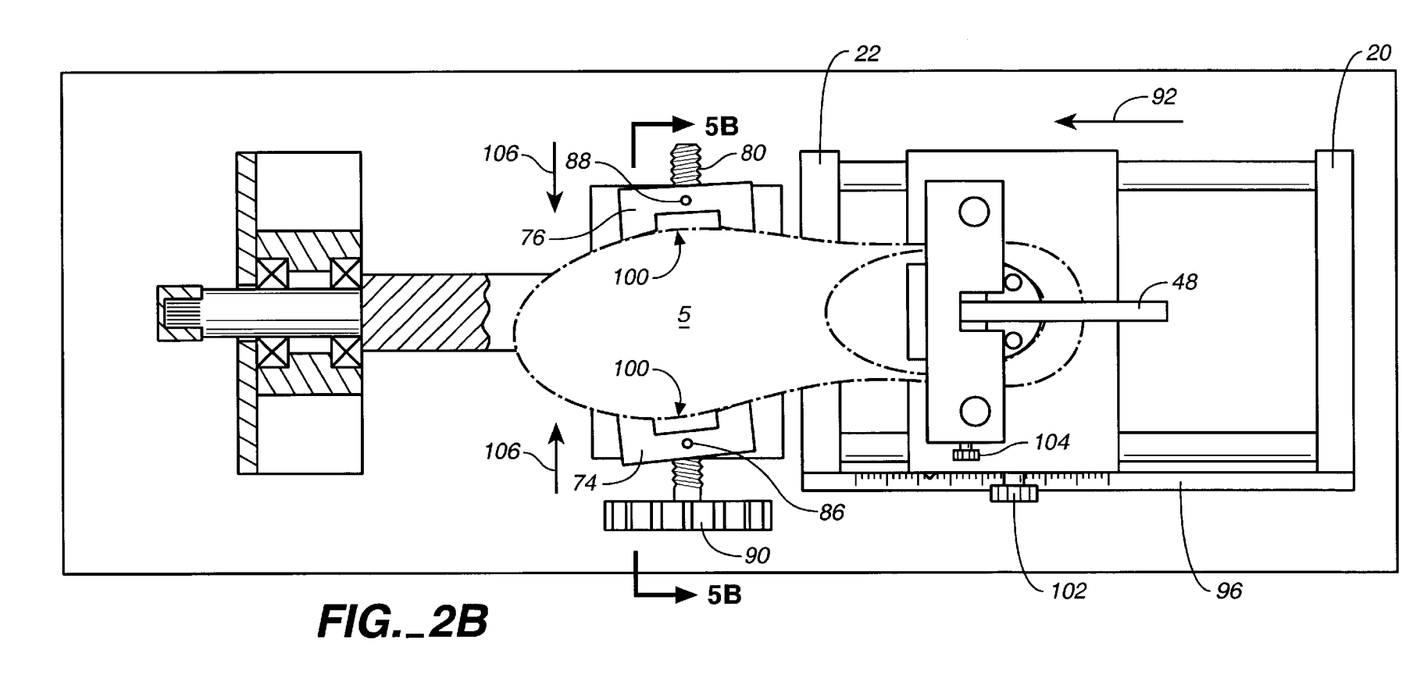
FIG. 2B is a partially cutaway top view of the invention, the cutaway portions being indicated at line 2B—2B in FIG. 3A.
Figure 3A:
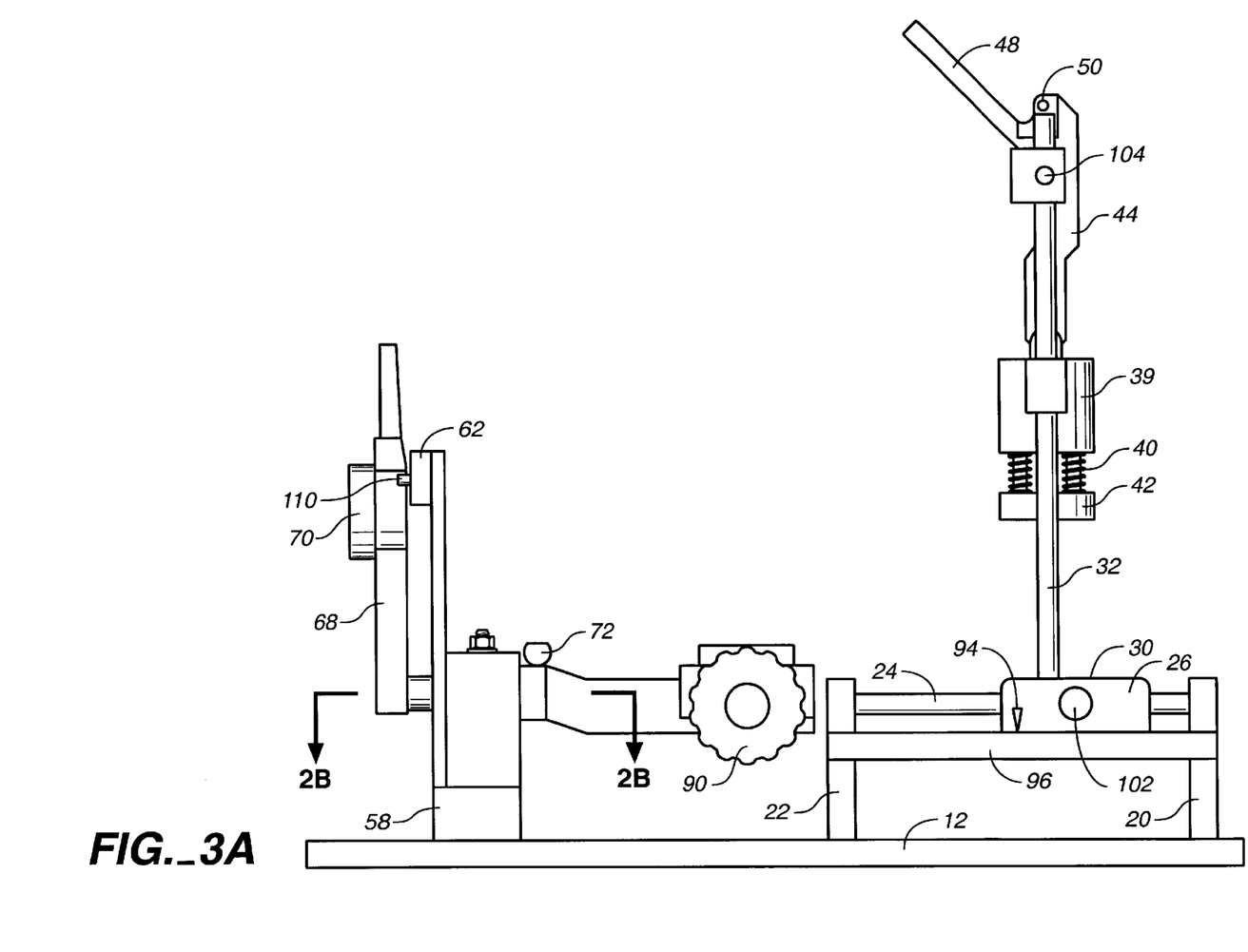
FIG. 3A is a side view of the preferred embodiment of the invention.
Figure 3B:
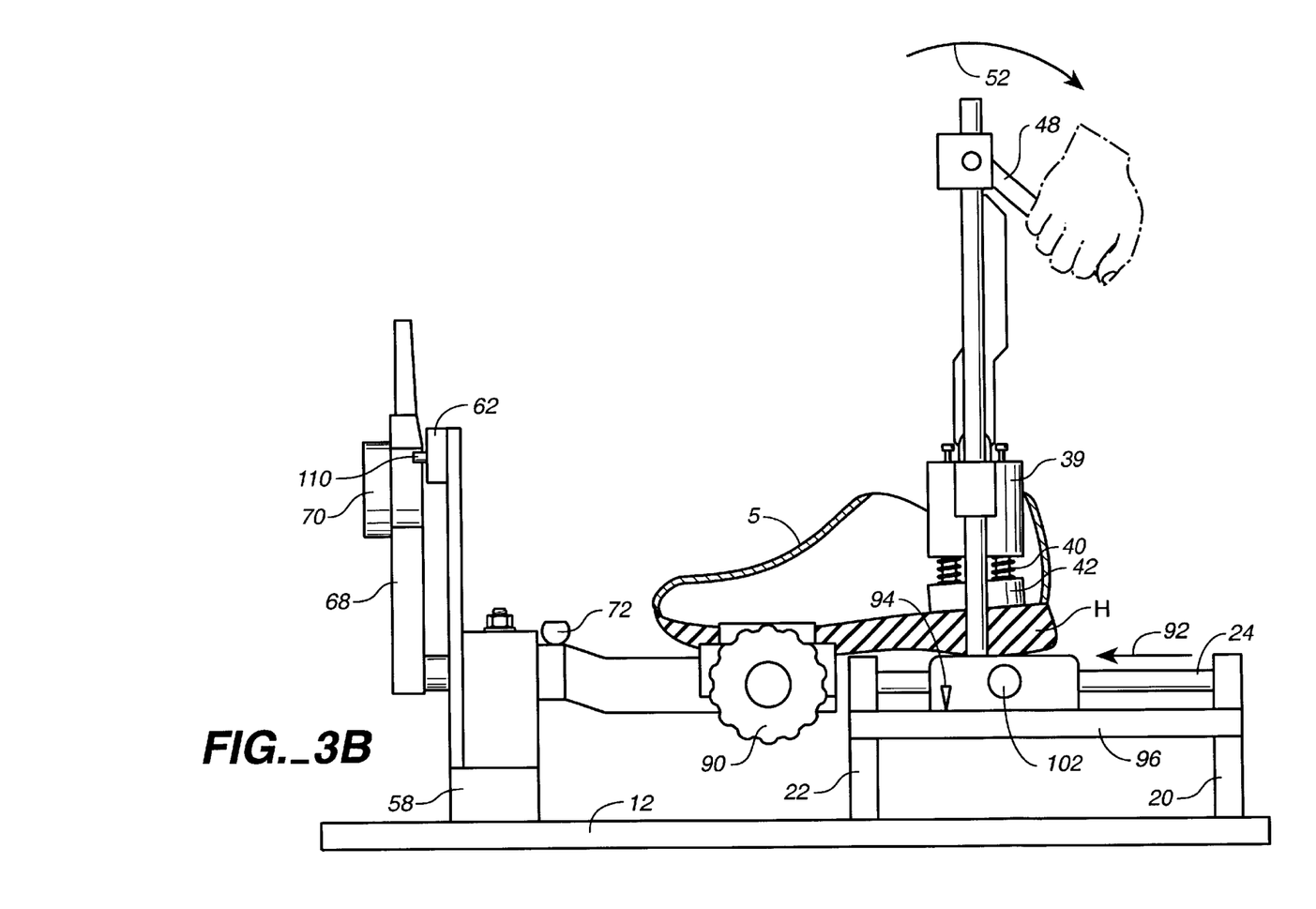
FIG. 3B is a side view similar to that of FIG. 3A with a cutaway view of a shoe clamped down on the fixed rear plate being slid forward to engage the laterally disposed forward clamps.

With the slidable heel block support portion 18 pulled to the rear 16 of the apparatus 10, such as is seen in FIG. 3A, the heel H of a shoe S is placed on the upper heel support plate surface 30 of the heel support plate 26. The heel press block mechanism 34 is then slid downwardly on the vertical heel press block rails 32 until the heel compression plate 42 is in snug contact with inner sole portion of the heel H of the shoe S. Heel press block mechanism set screw 104 is then tightened to frictionally engage one of the vertical heel press block rails 32. Second overeater cam lever portion 48 is then moved in the direction of first directional arrow 52 (seen in FIGS. 3B and 1) and as seen in FIG. 3B and as discussed above, upper heel press block rail and lever engaging portion 39, compression springs 40, and heel compression plate 42 are lowered further on the vertical heel press block rails 32, increasing pressure in the heel H of the shoe S against the upper heel support plate surface 30 until it is held firmly in place. The slidable heel block support portion 18 is then moved along rails 24 in the direction indicated by second directional arrow 92 (seen in FIGS. 2B and 3B). Note that on the side of heel support plate 26 there is an indicator 94. A sizing rail 96, which extends between the edges of heel block support rear plate 20 and heel block support front plate 22 has indicia, indicated at 98, thereon (seen in FIG. 2A). The indicia 98 and the indicator 94, cooperate to signal the size of the shoe being tested by the apparatus. When the ball portion of the shoe S, roughly indicated at 100 in FIG. 2B is in proper position to be engaged by clamps 74, 76 and the correct size is indicated on sizing rail 96 by indicator 94, a set screw knob 102 is tightened to frictionally engage the rail 24 and fix slidable heel block support portion 18 in the proper position.

Level 72 is checked to make sure that the axially rotatable shoe engaging portion is even. Now the first and second lateral shoe engaging clamps 74, 76 are brought into engagement with the shoe S. The clamp adjustment means knob 90 is turned and the attached partially threaded bolt 80 moves the two fixed clamp carriers 82, 84 that are attached to it together, as indicated by third directional arrows 106, seen in FIG. 2B. The first and second lateral shoe engaging clamps 74, 76 are pivoted, as indicated at 86 and 88, so that they will engage a variety of shoe sizes and configurations. Once they are brought into engagement, as seen in FIG. 2B, the torsion testing of the sample shoe can begin.

Figure 4A:
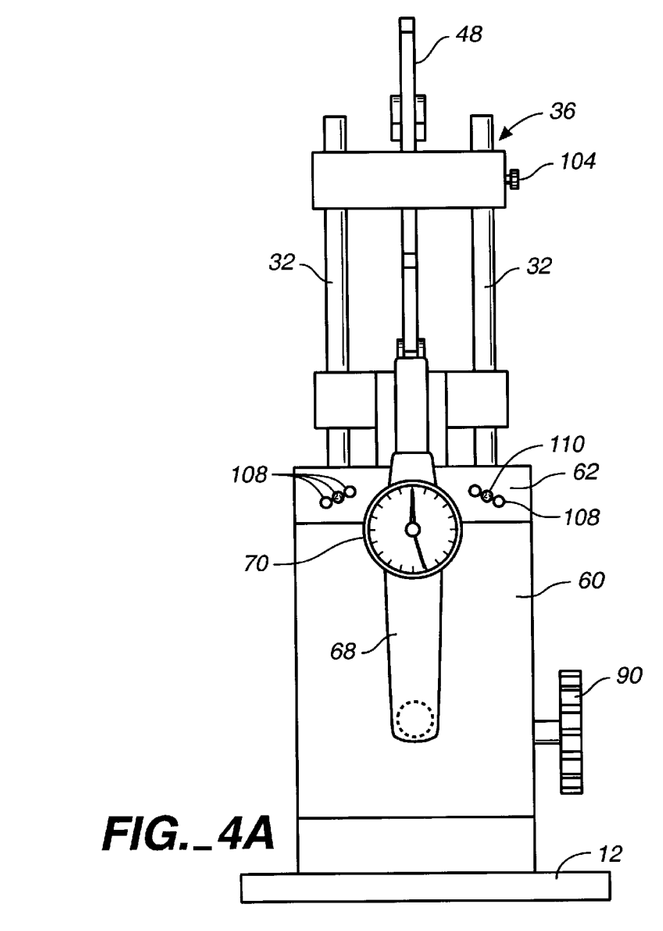
FIG. 4A is a front view of the invention with a shoe (not shown) engaged within the clamps and the torque meter at rest.
Figure 4B:
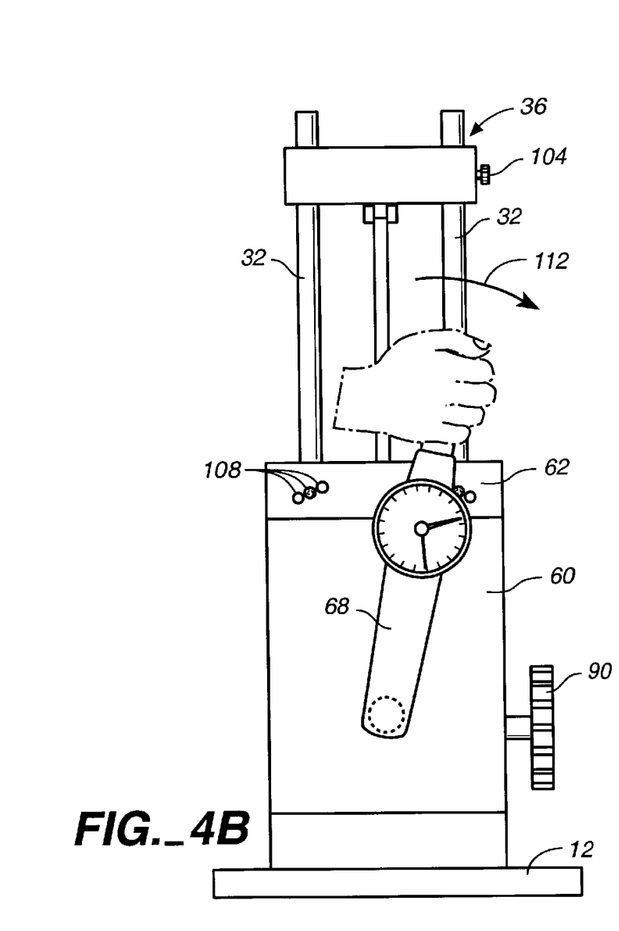
FIG. 4B is a front view of the invention with a shoe (not shown) engaged within the clamps and the torque meter pushed to the predetermined travel stop and the index reading showing on the dial.
Figure 5A:
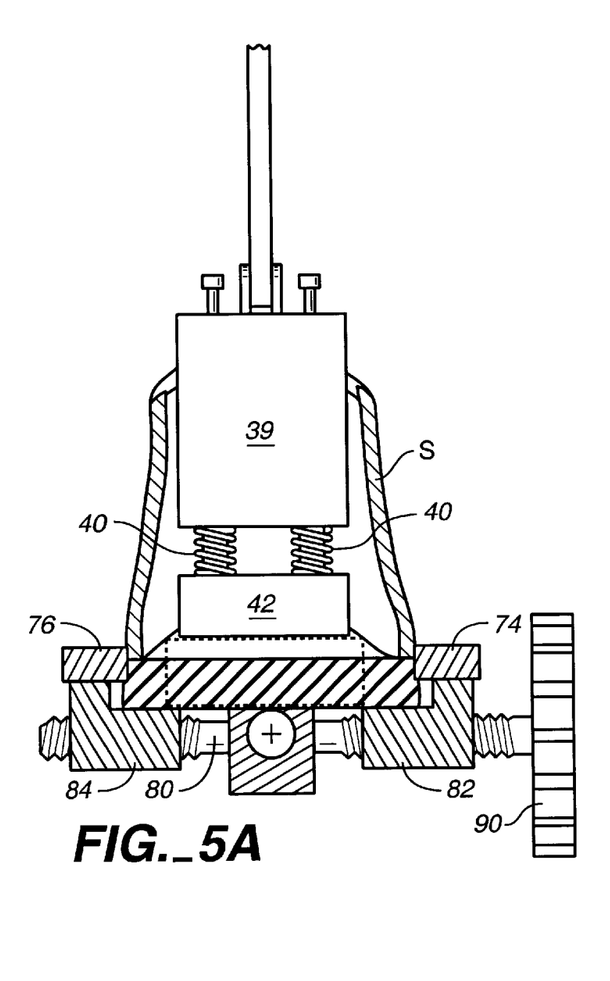
FIG. 5A is a partially cutaway view of the invention taken along the line 5—5 in FIG. 2B that generally corresponds to FIG. 4A with the shoe in place.
Figure 5B:
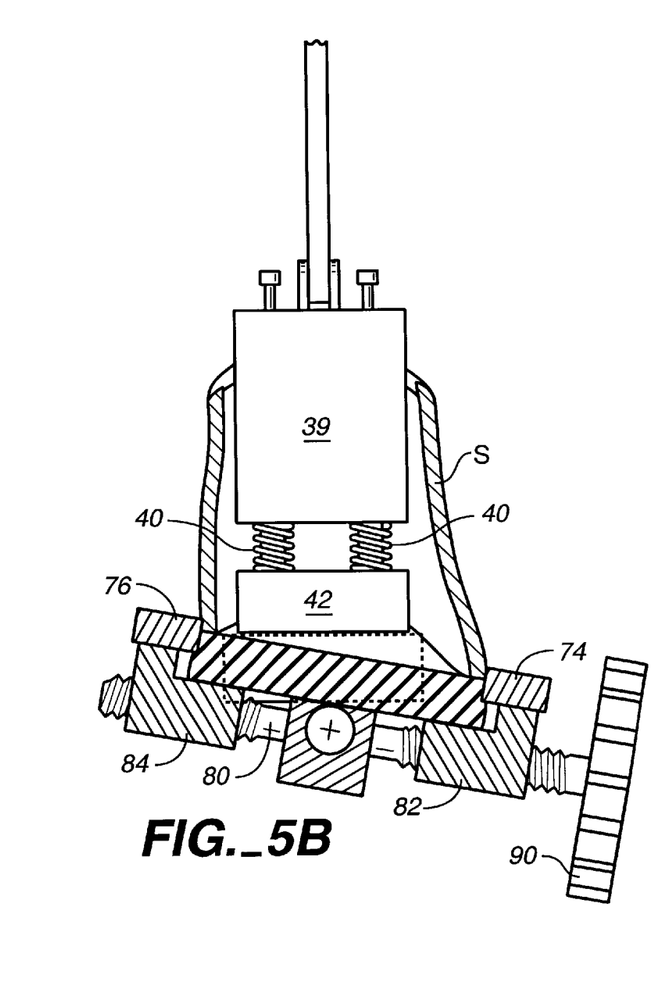
FIG. 5B is a partially cutaway view of the invention taken along line 5—5 in FIG. 2B that generally corresponds to FIG. 4B with the torque meter pushed to the predetermined travel stop.

Turning to FIGS. 4A and 4B, note that on travel stop support block 62 there are a plurality of travel stop apertures 108. In the embodiment seen and described herein there are three on each side of the torque meter 68. More or less could be used. They are there to allow the user to predetermine the angle at which they would like to measure the amount of recoil in the shoe S. Travel stops 110 (best seen in FIGS. 3A and 3B) are placed in the desired positions. The torque meter 68 is then moved, as indicated by the fourth directional arrow 112, and the meter dial 70 is read. It is contemplated that the meter dial would be calibrated in foot pounds or inch pounds, but it should be understood that any measure of force could be exhibited. Thus, an index can be developed for various shoes, shoe sizes, brands, and also the user can determine when the shoe is worn out and needs to be replaced.

The novel construction of the present invention simulates, by its action, the same type of stress that is generated during a stride while the wearer of the shoe is walking or running. There are three subphases in a stride. The first subphase is heel strike or contact, where the heel hits the ground. The second phase is midstance where the weight of the body is passing over the plantar surface of the foot, this is where pronation occurs. The third subphase is propulsion, where the toes are pushing off and, in a proper stride, the foot should be in a supinating position. It is known that if abnormal pronation is occurring, the midstance and propulsion subphases can possibly be prolonged and the weight transfer through the forefoot will be abnormal. This condition may lead to pain in the muscles in the bottom of the foot and in the heel. These symptoms can be alleviated with a more stable shoe, one that has less give in it during the midstance subphase of the stride. The present invention, when torque is applied to the shoe through the first and second lateral shoe engaging clamps 74, 76, attached at the position proximate where the head of the wearer's first and fifth metatarsal bones would be, simulate this midstance subphase torque. Thus, if a user is experiencing discomfort, a stiffer, more stable shoe can be provided.

It is apparent from the above that the present invention accomplishes all of the objectives set forth by providing a new and improved shoe testing apparatus and method for use that allows various brands of shoes or shoes of the same brand to be indexed according to their ability to resist twisting along their longitudinal axis. The instant invention will prove useful to athletes, casual sportspeople, athletic shoe outlets, podiatrists, sports medicine practitioners, and others.

With respect to the above description, it should be realized that the optimum dimensional relationships for the parts of the invention, to include variations in size, materials, shape, form, function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiment of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A shoe measuring apparatus to be used with a shoe having a heel, an inside heel, an inner heel surface, front side portions, and a longitudinal axis comprising:

a base;

a shoe heel support portion attached to said base, said shoe heel support portion including means for fixedly engaging the shoe heel;

a shoe front clamping portion attached to said base, said shoe front clamping portion fixedly engages the front side portions of the shoe, said shoe front clamping portion being axially rotatable about the longitudinal axis of the shoe; and a means for measuring torque including means for indicating the torque measurement; wherein said shoe front clamping portion is axially rotated to a predetermined position and said means for indicating the torque measurement indicates a measurement of torque created in the shoe.

2. The shoe measuring apparatus according to claim 1, wherein said shoe heel support portion further includes a slidable heel block support portion, said slidable heel block support portion being mounted on rails over said base, said rails extending between a heel block rear plate and a heel block front plate where said heel block rear plate and said heel block front plate are attached to said base, and where said slidable heel block support portion is slidable between said heel block rear plate and said heel block front plate and further where said slidable heel block support portion includes an upper heel support plate surface for engaging the heel of the shoe.

3. The shoe measuring apparatus according to claim 2, wherein said shoe heel support portion includes a pair of vertical heel press block rails extending upwardly from said upper heel support plate surface, said vertical heel press rails engaging a heel press block mechanism slidable on said vertical heel press rails, said heel press block mechanism further including a heel compression plate adapted to fit inside the shoe and press the heel of the shoe onto said upper heel support plate surface.

4. The shoe measuring apparatus according to claim 3, further including an overeater cam lever attached to said heel compression plate, where activating said overeater cam lever further presses said heel compression plate against the inside heel of the shoe, further pressing the heel against said upper heel support plate surface.

5. The shoe measuring apparatus according to claim 4, where said heel compression plate further includes a plurality of compression springs configured to hold said heel compression plate firmly against the inner heel surface of the shoe.

6. The shoe measuring apparatus according to claim 5, further including a fixed portion attached to said base, said fixed portion supporting an upwardly disposed torque support plate, said torque support plate including an aperture through which said axially rotatable shoe front clamping portion passes and is supported.

7. The shoe measuring apparatus according to claim 6, wherein said axially rotatable shoe front clamping portion extends on one side from said upwardly disposed torque support plate towards said shoe heel support portion and on an other side of said upwardly disposed torque support plate terminates in said means for measuring torque.

8. The shoe measuring apparatus according to claim 7, wherein said axially rotatable shoe front clamping portion extended towards said shoe heel support portion includes a pair of inwardly opening C-shaped clamps disposed parallel to said base.

9. The shoe measuring apparatus according to claim 8, wherein said C-shaped clamps include adjustment means, said adjustment means permitting the distance between said C-shaped clamps to be changed.

10. The shoe measuring apparatus according to claim 9, wherein said adjustment means comprises a threaded bolt fixedly attached to a pair of clamp carriers, each said clamp carrier being further engaged to one of said C-shaped clamps.

11. The shoe measuring apparatus according to claim 10, wherein said C-shaped clamps are pivotally attached to said clamp carriers.

12. A shoe measuring apparatus to be used with a shoe having a heel, front side portions and an inner heel composing;
   a base;
   a shoe heel support portion attached to said base, said shoe heel support portion including means for fixedly engage a shoe heel, said shoe heel support portion further including a slidable heel block support portion, said slidable heel block support portion being mounted on rails over said base, said rails extending between a heel block rear plate and a heel block front plate where said heel block rear plate and said heel block front plate are attached to said base, and where said slidable heel block support portion is slidable between said heel block rear plate and said heel block front plate and further where said slidable heel block support portion includes an upper heel support plate surface for engaging the heel of the shoe and further where said shoe heel support portion fixed heel engagement means includes a pair of vertical heel press block rails extending upwardly from said upper heel support plate surface, said vertical heel press rails engaging a heel press block mechanism slidable on said vertical heel press rails, said heel press block mechanism further including a heel compression plate adapted to fit inside the shoe and press the heel of the shoe onto said upper heel support plate surface said shoe heel support portion further including an overeater cam lever attached to said heel compression plate, where activating said overeater cam lever further presses said heel compression plate against the inside heel of the shoe, further pressing the heel against said upper heel support plate surface and where said heel compression plate further includes a plurality of compression springs configured to hold said heel compression plate firmly against the inner heel of the shoe;
   a shoe front clamping portion attached to said base, said shoe front clamping portion fixedly engages the front side portions of the shoe, said shoe front clamping portion being axially rotatable about a longitudinal axis of the shoe; and
   a means for measuring torque including means for indicating the torque measurement; wherein said shoe front clamping portion is axially rotated to a predetermined position and said means for indicating the torque measurement indicates a measurement of torque created in the shoe.

13. The shoe measuring apparatus according to claim 12, further including a fixed portion attached to said base, said fixed portion supporting an upwardly disposed torque support plate, said torque support plate including an aperture through which said axially rotatable shoe front clamping portion passes and is supported.

14. The shoe measuring apparatus according to claim 13, wherein said axially rotatable shoe front clamping portion extends on one side from said upwardly disposed torque support plate towards said shoe heel support portion and on an other side of said upwardly disposed torque support plate terminates in said means for measuring torque.

15. The shoe measuring apparatus according to claim 14, wherein said axially rotatable shoe front clamping portion extended towards said shoe heel support portion includes a pair of inwardly opening C-shaped clamps disposed parallel to said base.

16. The shoe measuring apparatus according to claim 15, wherein said C-shaped clamps include adjustment means adapted to change the distance between them.

17. The shoe measuring apparatus according to claim 16, wherein said adjustment means comprises a threaded bolt fixedly attached to a pair of clamp carriers, each said clamp carrier being further engaged to one of said C-shaped clamps.

18. The shoe measuring apparatus according to claim 17, wherein said C-shaped clamps are pivotally attached to said clamp carriers.

19. A method for measuring a longitudinal axial flex of a shoe having a heel and a front portion comprising the steps of:
   providing a planar platform;
   fixedly engaging the heel of the shoe with said planar platform;
   providing an axially rotatable clamping means to engage the front portion of the shoe;
   fixedly and laterally engaging the front portion of the shoe with said axially rotatable clamping means;
   providing a means for measuring torque attached to said axially rotatable clamping means;
   axially rotating the clamped front portion of the shoe in relation to the fixed heel portion of the shoe;
   observing said means for measuring torque.

20. The method of claim 19, further comprising the step of:
   providing a visual torque readout means on said means for measuring torque.

* * * * *